United States Patent
Bassett et al.

[11] Patent Number: 5,842,865
[45] Date of Patent: Dec. 1, 1998

[54] SELF-TAPPING IMPLANT WITH MULTIPLE CONCAVE TAPPING CHANNELS

[75] Inventors: Jeffrey A. Bassett, Vista; Jeffrey D. Lueschen, Carlsbad, both of Calif.

[73] Assignee: Sulzer Calcitek Inc., Carlsbad, Calif.

[21] Appl. No.: 928,930

[22] Filed: Sep. 12, 1997

[51] Int. Cl.⁶ .................................................. A61C 8/00
[52] U.S. Cl. .............................................. 433/174; 606/73
[58] Field of Search .................................. 433/172, 173, 433/174, 175, 176; 606/73, 80; 411/387, 418, 420, 421

[56] References Cited

U.S. PATENT DOCUMENTS

| | | | |
|---|---|---|---|
| Re. 31,948 | 7/1985 | Deutsch et al. | 433/221 |
| Re. 33,796 | 1/1992 | Niznick | 433/173 |
| Re. 34,871 | 3/1995 | McGuire et al. | 606/73 |
| D. 273,984 | 5/1984 | Vlock | 433/225 |
| D. 296,362 | 6/1988 | Branemark | D24/33 |
| D. 330,767 | 11/1992 | Jorneus | D24/156 |
| D. 342,314 | 12/1993 | Miller | D24/156 |
| D. 356,868 | 3/1995 | Broberg et al. | D24/156 |
| 3,067,740 | 12/1962 | Haboush . | |
| 3,218,656 | 11/1965 | Reiland | 411/418 |
| 3,488,779 | 1/1970 | Christensen . | |
| 3,579,831 | 5/1971 | Stevens et al. . | |
| 3,732,621 | 5/1973 | Bostrom . | |
| 3,846,846 | 11/1974 | Fischer . | |
| 3,982,464 | 9/1976 | Sygnator | 411/387 |
| 4,125,050 | 11/1978 | Schwartzman et al. | 411/387 |
| 4,145,764 | 3/1979 | Suzuki et al. . | |
| 4,185,383 | 1/1980 | Heimke et al. | 433/173 |
| 4,187,611 | 2/1980 | Chan | 433/225 |
| 4,253,833 | 3/1981 | Edelman | 433/173 |
| 4,324,550 | 4/1982 | Reuther et al. | 433/174 |
| 4,365,958 | 12/1982 | Vlock | 433/225 |
| 4,406,623 | 9/1983 | Grafelmann et al. | 433/174 |
| 4,407,620 | 10/1983 | Shinjo | 411/387 |
| 4,463,753 | 8/1984 | Gustillo . | |
| 4,468,200 | 8/1984 | Munch | 433/174 |
| 4,479,783 | 10/1984 | Weissman | 433/221 |
| 4,484,570 | 11/1984 | Sutter et al. . | |
| 4,495,664 | 1/1985 | Blanquaert . | |
| 4,511,335 | 4/1985 | Tatum, Jr. | 433/173 |
| 4,531,915 | 7/1985 | Tatum, Jr. | 433/173 |
| 4,535,487 | 8/1985 | Esper et al. | 623/22 |
| 4,547,157 | 10/1985 | Driskell | 433/173 |
| 4,645,453 | 2/1987 | Niznick | 433/173 |
| 4,713,004 | 12/1987 | Linkow et al. | 433/174 |
| 4,730,969 | 3/1988 | Dohi | 411/387 |
| 4,781,506 | 11/1988 | Roberts et al. | 411/387 |
| 4,826,434 | 5/1989 | Krueger | 433/174 |
| 4,842,518 | 6/1989 | Linkow et al. | 433/174 |
| 4,851,008 | 7/1989 | Johnson | 623/16 |
| 4,863,383 | 9/1989 | Grafelmann | 433/174 |
| 4,871,313 | 10/1989 | Maillefer | 433/225 |
| 4,878,915 | 11/1989 | Brantigan | 623/17 |
| 4,932,868 | 6/1990 | Linkow et al. | 433/174 |
| 5,000,686 | 3/1991 | Lazzara et al. | 433/174 |

(List continued on next page.)

FOREIGN PATENT DOCUMENTS

| | | |
|---|---|---|
| 0 139 052 | 10/1983 | European Pat. Off. . |
| 0237505 | 11/1987 | European Pat. Off. . |
| 0 323 559 | 11/1988 | European Pat. Off. . |
| 30 43 336 | 6/1981 | Germany . |
| 32 41 963 | 4/1984 | Germany . |
| 85 23 007 U | 11/1985 | Germany . |
| 36 26172A1 | 2/1988 | Germany . |
| 332 486 | 2/1971 | Sweden . |

OTHER PUBLICATIONS

3i Implant Innovations; 1995; *Speed and Control.*
Vermont Tap & Die; *TAPS Technical Information.*

*Primary Examiner*—Cary E. O'Connor
*Attorney, Agent, or Firm*—Philip S. Lyren

[57] ABSTRACT

A self-tapping implant for implantation into bone. The implant includes multiple flutes disposed around its tapping end. Each flute includes three separate concave cavities working in conjunction to tap the bone. A first cavity provides a primary cutting edge; a second cavity provides a repository for bone chips; and a third cavity provides both cutting and storing of bone.

48 Claims, 2 Drawing Sheets

U.S. PATENT DOCUMENTS

| | | | |
|---|---|---|---|
| 5,061,181 | 10/1991 | Niznick | 433/174 |
| 5,064,425 | 11/1991 | Branemark et al. | 606/72 |
| 5,074,790 | 12/1991 | Bauer | 433/174 |
| 5,078,607 | 1/1992 | Niznick | 433/174 |
| 5,087,201 | 2/1992 | Mondani et al. | 433/174 |
| 5,166,225 | 11/1992 | Riera | 433/516 |
| 5,167,664 | 12/1992 | Hodorek | 606/73 |
| 5,194,000 | 3/1993 | Dury | 433/173 |
| 5,205,746 | 4/1993 | Chanavaz | 433/174 |
| 5,246,369 | 9/1993 | Poulmaire | 433/173 |
| 5,269,685 | 12/1993 | Jorneus et al. | 433/174 |
| 5,300,076 | 4/1994 | Leriche | 606/73 |
| 5,312,254 | 5/1994 | Rosenlicht | 433/173 |
| 5,312,256 | 5/1994 | Scortecci | 433/174 |
| 5,324,199 | 6/1994 | Branemark | 433/174 |
| 5,338,197 | 8/1994 | Kwan | 433/174 |
| 5,366,374 | 11/1994 | Vlassis | 433/165 |
| 5,370,662 | 12/1994 | Stone et al. | 606/232 |
| 5,376,004 | 12/1994 | Mena | 433/173 |
| 5,417,692 | 5/1995 | Goble et al. | 606/73 |
| 5,427,527 | 6/1995 | Niznick et al. | 433/174 |
| 5,435,723 | 7/1995 | O'Brien | 433/174 |
| 5,468,149 | 11/1995 | D'Alise | 433/173 |
| 5,484,285 | 1/1996 | Morgan et al. | 433/173 |
| 5,489,210 | 2/1996 | Hanosh | 433/173 |
| 5,503,558 | 4/1996 | Clokie | 433/173 |
| 5,522,843 | 6/1996 | Zang | 606/232 |
| 5,527,183 | 6/1996 | O'Brien | 433/174 |
| 5,601,429 | 2/1997 | Blacklock | 433/174 |

SELF-TAPPING IMPLANT WITH MULTIPLE CONCAVE TAPPING CHANNELS

BACKGROUND OF THE INVENTION

Self-tapping implants are designed to be implanted directly within bone. During a typical surgical implantation procedure, the implantation site is exposed; and a hole is drilled into the bone. The end of the implant is then positioned into the hole and the implant is screwed downwardly to the desired position. As the implant rotates, it simultaneously taps threads and screws into these threads.

A typical self-tapping implant has a first end for tapping threads in the bone, a second end for connecting to a prosthesis, and a threaded middle section for engaging the threads tapped in the bone. The tapping end of the implant usually consists of several grooves or flutes that extend upwardly on the sidewall of the implant along the longitudinal axis. Each flute includes a cutting edge that scrapes off bone as the implant is rotated into the hole. The cutting edges form threads along the bone for engaging the threaded section of the implant.

Present self-tapping implants offer many advantages over other implants. First, a separate bone tapping tool is not required since the implant taps the bone. Second, the overall time to perform the surgical implantation procedure is reduced since the bone does not first have to be separately tapped before the implant is inserted into the hole. As another advantage, self tapping implants create a more intimate contact with the surrounding bone and thus improve stability and conditions for oseointegration.

In spite of the foregoing advantages, present self-tapping implants also possess numerous disadvantages. As one disadvantage, an excessive amount of torque is required in order to screw the implant into the bone. The flutes at the tapping end of the implant usually have a single cutting edge or surface typically formed having a right angle junction with the threads. Cutting edges formed from a right angle junction, however, do not simultaneously maximize cutting performance and minimize torsional forces required to insert the implant.

As another disadvantage, the right angle junction between the threads and the cutting edge has an abrupt corner. When the implant is being tapped, bone chips flow unevenly over this corner. Additionally, bone chips tend to clog around the cutting edge.

As a further disadvantage, some prior self-tapping implants have a small clearance surface or a slight bevel adjacent the cutting edge. This clearance surface provides some clearance for bone chips after they are cut from the bone during tapping. The geometry of this surface, though, is not sufficient to provide clearance for large bone chips or sufficient to accumulate a significant volume of bone chips.

As yet another disadvantage, the cutting edge should make a smooth transition to the tapping end of the implant. A smooth transition would cause the cutting edge to gradually engage the implantation site and enable tapping to initiate with less of a downward force.

As yet another disadvantage, the tapping end of the implant should have a geometry to cut bone chips and direct them away from the primary cutting edge. Further, the tapping end should be configured to facilitate insertion of the implant into the implantation site.

SUMMARY OF THE INVENTION

The present invention is directed toward a self-tapping implant that screws into a hole in bone. The implant comprises a first end for tapping threads into bone, a second end, and a threaded middle section for engaging the threads tapped into the bone. The tapping end has separate flutes, and each flute includes multiple cavities. In the preferred embodiment, the implant has three separate flutes; and each flute has three separate and distinct cavities. The configuration of the tapping end provides numerous advantages.

One important advantage of the present invention is that the implant has multiple flutes with multiple distinct cavities within each flute. The cavities work together to minimize the torque needed to insert the implant into bone. In an embodiment having three cavities, the first cavity forms the primary cutting edge for tapping the bone. The second cavity provides a volume adjacent the first cavity for accumulating bone chips. The third cavity directs bone chips away from the cutting edges and prevents bone from clogging around the implant. The third cavity also has a cutting edge to aid the primary cutting edge and to initially tap bone as the end of the implant is first inserted into the implantation site.

As another advantage, the first cavity has a continuous curve configuration descending downwardly from the cutting edge. This curvature directs a smooth flow of bone chips from the cutting edge. Preferably, each of the cavities has a generally concave configuration.

As another advantage, the second cavity functions to relieve the first cavity. The second cavity provides a relatively large clearance for bone chips after they are cut from the bone during tapping. Further, the geometry of this cavity is concave and has a sufficient size to provide clearance for larger bone chips and to accumulate a significant volume of bone chips.

As a further advantage, the tapping end of the implant has a configuration that facilitates the insertion of the implant into the implantation sight. Furthermore, the cavities intersect this end so as to gradually introduce them into the implantation site. The tapping end thus makes a smooth transition into the implantation site and reduces the downward force required to insert the implant.

As still another advantage, the configuration of the tapping end cuts and draws bone chips away from the cutting edges. The cutting edge thus do not become clogged or congested with bone chips.

The invention, accordingly, comprises the apparatus possessing the construction, combination of elements, and arrangement of parts which are exemplified in the following detailed description. For a fuller understanding of the nature and objects of the invention, reference should be made to the following detailed description taken in connection with the accompanying drawings.

DETAILED DESCRIPTION OF THE PREFERRED EMBODIMENTS

Figure 1:
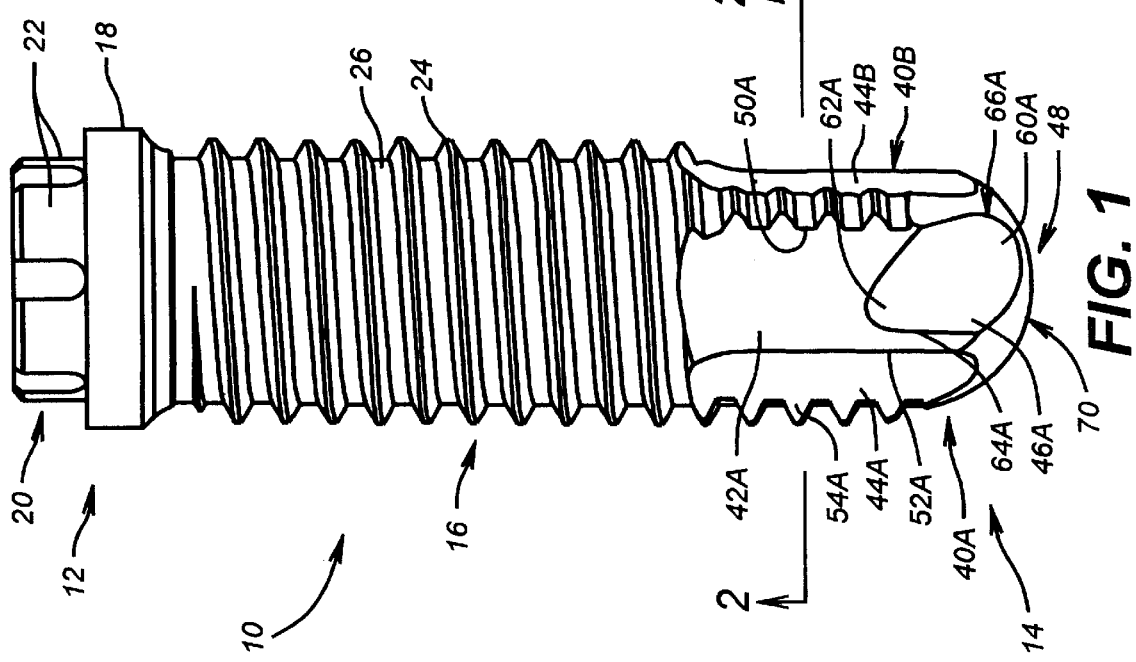
FIG. 1 is an elevational view of a self-tapping implant according to the invention.

FIG. 1 shows a self-tapping implant generally at 10. Implant 10 includes a first end 12, a second end 14 oppositely disposed from the first end, and a threaded middle section 16 disposed between the two ends. The implant may be any one of various dental implants known to those skilled in the art and designed to be implanted into bone. Implant 10 is shown as a dental implant and preferably is formed from titanium alloy and may have any one of various surface coatings, such as an as-machined surface or microtextured surface.

End 12 includes an interface ring 18 that is slightly tapered. A prosthetic interface 20 extends upwardly from interface ring 18. The prosthetic interface includes a plurality of spline tines 22 for engaging a dental prosthesis (not shown). These spline tines are taught in U.S. Pat. No. 5,449,291 entitled "Dental Implant Assembly Having Tactile Feedback" issued to Lueschen et al.; this patent is fully incorporated herein by reference.

Threaded middle section 16 is disposed between end 12 and end 14. This section includes threads 24 that circumferentially extend around a cylindrical body portion 26 of implant 10.

Figure 2:
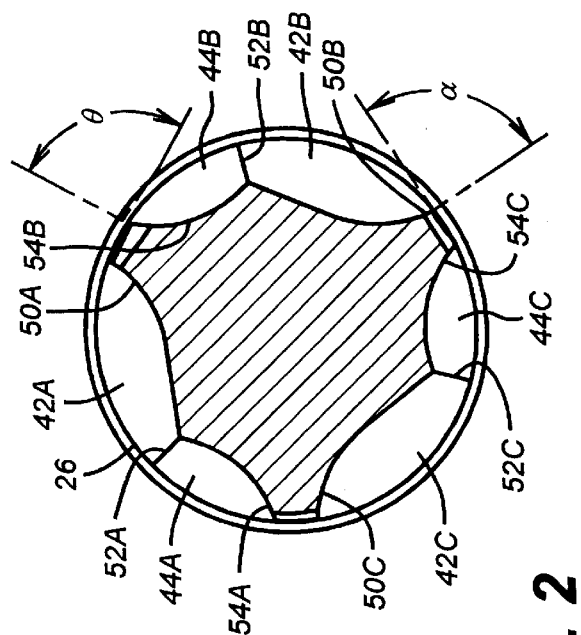
FIG. 2 is a cross-sectional view of the implant of FIG. 1 taken through line 2—2.
Figure 3:
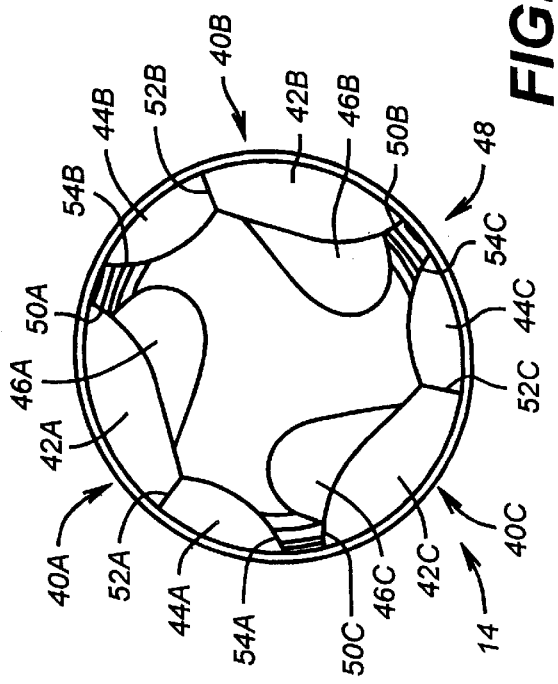
FIG. 3 is an end view of the implant of FIG. 1.

Reference is now simultaneously made to FIGS. 1–3. End 14 is the tapping end of implant 10. In the preferred embodiment, this end includes three separate flute sections shown as 40A, 40B, and 40C, respectively. Each flute section additionally includes three separate and distinct cavities or surfaces 42, 44, and 46 with letters A, B, and C corresponding to a particular flute section.

Flutes 40A, 40B, and 40C extend upwardly in a longitudinal direction from a spherical distal portion 48 of end 14. These flutes are disposed around body portion 26 and are symmetrically spaced about end 14. Further, each flute is configured similarly, with the details of flute section of 40A more fully discussed below and shown completely in FIG. 1.

Looking primarily to flute section 40A, cavity 42A includes a primary cutting edge 50A. This edge has a long, straight edge that runs parallel to the longitudinal axis of body portion 26. Cavity 42A has a continuous curvature that descends downwardly from cutting edge 50A and then upwardly to a border 52A that forms a transition between cavities 42A and 44A. This curvature preferably has a concave or curved configuration. This configuration does not have any abrupt corners or edges and hence is more gentle so as to direct a smooth flow of bone chips away from cutting edge 50A.

Cavity 44A has an elongated configuration that runs parallel and adjacent to cavity 42A. Cavity 44A also preferably has a concave or curved configuration. This configuration has a smooth curvature from border 52A on one side to edge 54A on a oppositely disposed side. The concave configuration directs a smooth flow of bone chips into cavity 44A.

Cavity 44A provides relief to cavity 42A and cutting edge 50A. In particular, the size of cavity 44A provides clearance for large bone chips and provides an area for accumulating a relatively large volume of bone chips.

Cavity 46A has a concave or curved configuration with a spiral point shape. The spiral point has an angulation that is opposite to threads 24. Further, as best shown in FIG. 1, cavity 46A has a spherical end 60A on one side and a conical end 62A on an oppositely disposed side. End 62A extends upwardly into cavity 42A and forms a border 64A between the two cavities. A cutting edge 66A extends along one side of cavity 46A.

End 14 has a spherical configuration at its proximal portion 70. Cavities 42A, 44A, and 46A intersect end 14 and extend partly into this proximal portion. The intersection of these cavities causes a gradual introduction of cutting edges 50 and 66 into the implantation site. As such, a smooth transition occurs as the implant begins to tap bone. This smooth transition further reduces the downward force required to be exerted on implant 10 during tapping. Additionally, the spherical configuration pilots end 14 into the implantation sight and also helps ensure that implant 10 maintains proper alignment as it is rotated.

During tapping, end 14 is inserted into the implantation site in bone, and implant 10 is rotated in a clockwise direction. Cutting edge 66 initially cuts or scrapes bone chips from surrounding bone. This edge performs the first cutting operation before cutting edge 50 commences primary cutting. As the implant is rotated, cavity 46 draws bone chips away from cutting edges 50 and 66. The movement of these bone chips away from cutting edge 50, in particular, prevents unwanted clogging or accumulation of chips at the primary cutting edge.

As cavity 42 enters the implantation sight, cutting edge 50 begins the primary cutting of bone. Bone chips flow smoothly from cavity 42, over border 52, and collect in cavity 44. The concave configuration of cavity 44 allows a greater volume of bone to accumulate and helps to maintain cutting edge 50 free from bone chips that may clog the area or otherwise inhibit cutting operations. The area immediately adjacent cutting edge 50 is thus substantially free from cut bone chips. As such, the interference or collision between cut bone chips and the cutting edge is greatly minimized.

FIG. 2 illustrates two angles $\theta$ and $\alpha$. Angle $\theta$ is formed between a tangent to the outer circumference of threads 26 and a tangent to edge 54. Angle $\alpha$ is formed between a tangent to threads 26 and a tangent to edge 50. Preferably, these angles do not form right angles and rather form obtuse or acute angles. Some examples of these angles are as follows: (1) for a 3.75 mm dental implant $\theta=112°$ and $\alpha=101°$; and (2) for a 5.0 mm dental implant $\theta=94°$ and $\alpha=81°$.

Figure 5:
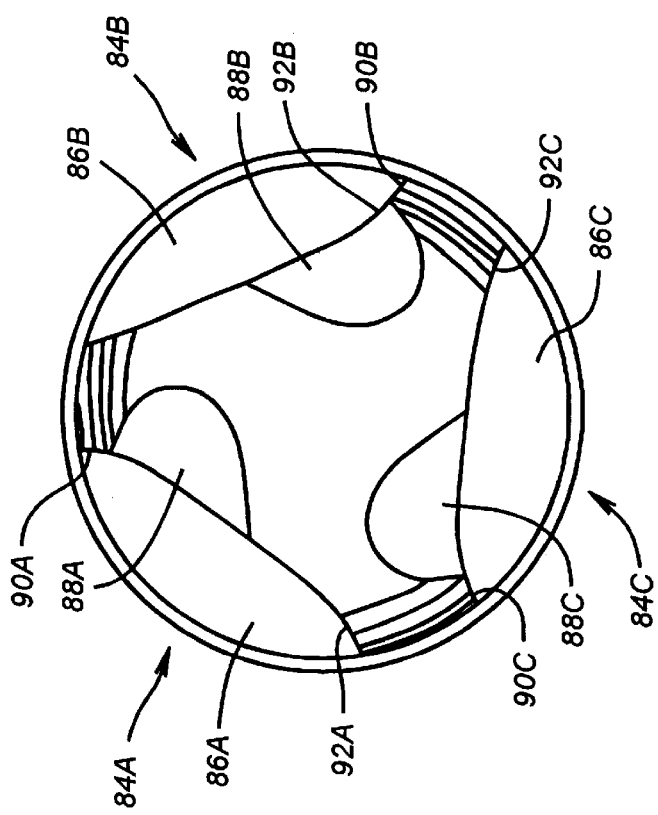
FIG. 5 is an end view of the implant of FIG. 4.
Figure 4:
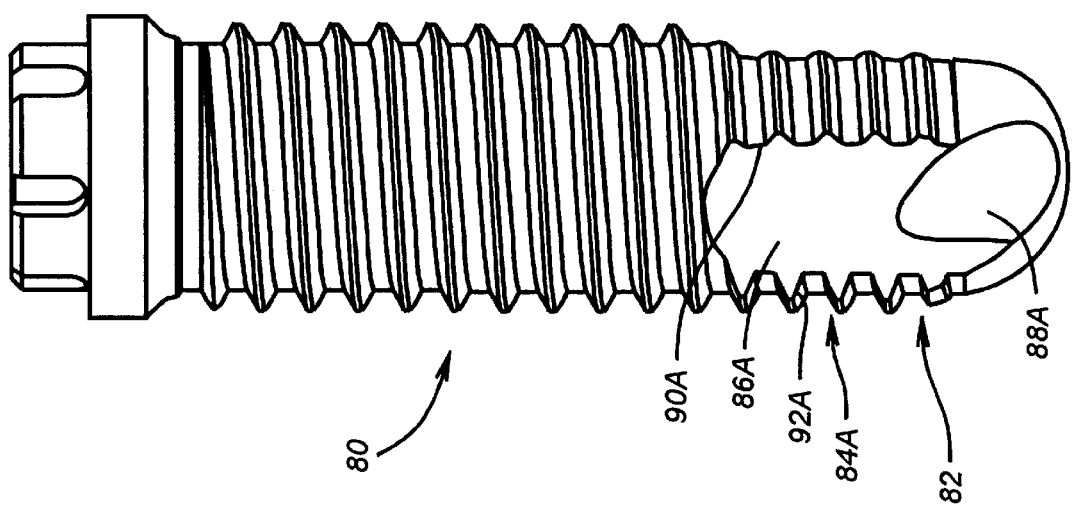
FIG. 4 is a plan view of an alternate embodiment of the implant of FIG. 1.

FIGS. 4 and 5 show an alternate implant 80 to implant 10 of FIG. 1. The primary difference between these two implants is implant 10 has three cavities per flute whereas implant 80 has two cavities per flute.

Implant 80 includes a tapping end 82 that has three separate flute sections 84A, 84B, and 84C. Flute section 84A is shown in FIG. 4 and is representative of the other flute sections. Flute section 84A includes two separate and distinct cavities 86A and 88A (FIG. 5 shows these cavities for flute sections 84B and 84C). Cavity 88A is similarly configured to cavity 46A of FIG. 1, previously described herein. Cavity 86A has a primary cutting edge 90A that is similarly configured to cutting edge 50 in FIG. 1. The cavity has a continuous curvature that smoothly descends downwardly from cutting edge 90A and then upwardly to surface 92A to form a concave or curved shaped cavity. The general curvature of cavity 86A is similar to cavity 46A of FIG. 1; yet the overall volume of cavity 86A is relatively larger. This added volume provides additional space for bone chips and helps keep cutting edge 90A from becoming clog during tapping.

FIGS. 2, 3, and 5 show an implant that has three different flute sections disposed about the tapping end. The number of flute sections may vary, and three are shown to illustrate the preferred embodiment. An implant having a larger diameter, for example, may require four or five different flute sections disposed about the tapping end. Alternatively, an implant having one or two flutes about the tapping end is within the scope of this invention.

Since certain changes may be made in the above-described apparatus without departing from the scope of the invention herein involved, all matter contained in the description or shown in the accompanying drawings shall be interpreted as illustrative and not in a limiting sense.

The invention claimed is:

1. A self-tapping implant for permanently anchoring in bone, comprising:
   a generally cylindrically shaped body having an externally threaded middle section and an end adjacent said middle section, wherein said end includes three separate flutes disposed around said body with each of said flutes having three separate and distinct cavities for tapping said bone, wherein said three cavities are continuous for directing bone chips into each of said cavities.

2. The self-tapping implant of claim 1 in which:
   a first cavity has a generally concave configuration with a primary cutting edge for removing bone chips from said bone and being disposed along a longitudinal axis of said body; and
   a second cavity is adjacent said first cavity to provide clearance for said bone chips.

3. The self-tapping implant of claim 1 in which:
   a first cavity includes a primary cutting edge; and
   a second cavity is adjacent said first cavity and has a concave configuration.

4. The self-tapping implant of claim 3 in which said cutting edge removes bone chips from said bone and said bone chips move from said first cavity and then into said second cavity.

5. The self-tapping implant of claim 1 in which:
   a first cavity includes a primary cutting edge for removing bone chips from said bone;
   a second cavity is adjacent said first cavity and accumulates said bone chips; and
   a third cavity is adjacent said first cavity.

6. The self-tapping implant of claim 5 in which said third cavity has an edge that removes bone chips from said bone.

7. The self-tapping implant of claim 5 in which said third cavity directs said bone chips away from said cutting edge.

8. An implant, comprising:
   a generally elongated body having external threads disposed along a midsection and a tapping end adjacent said midsection, wherein said tapping end taps bone as said implant is screwed into said bone, said tapping end includes at least two flutes each having a first cavity with a primary cutting edge and a second cavity adjacent to and connected to said first cavity and having a secondary cutting edge continuous with said primary cutting edge.

9. The implant of claim 8 which said first cavity has a concave configuration and an edge for cutting said bone.

10. The implant of claim 8 in which:
    said first cavity has an elongated configuration extending along a longitudinal axis of said implant, and said cutting edge is disposed along one side of said first cavity and positioned to remove said bone chips from said bone as said implant is screwed into said bone; and
    said second cavity has a volume for accumulating said bone chips removed from said bone.

11. The implant of claim 8 further comprising an elongated third cavity adjacent said first cavity, wherein said third cavity has a volume for accumulating bone chips removed from said bone.

12. The implant of claim 8 in which:
    said tapping end includes a spherical tip; and
    said flutes are symmetrically positioned around said tapping end and extend from said spherical tip toward said midsection.

13. A self-tapping implant for anchoring in bone, comprising:
    an elongated body having a threaded midsection and a tapping end including at least one flute formed having at least two separate and distinct cavities for tapping bone, wherein said two cavities are connected together for directing bone chips through each of said cavities.

14. The self-tapping implant of claim 13 in which said two separate and distinct cavities include:
    a first cavity having a cutting edge for removing bone chips from said bone as said implant is screwed into said bone; and
    a second cavity being disposed next to said first cavity to collect said bone chips.

15. The self-tapping implant of claim 14 in which said bone chips move away from said cutting edge to said second cavity.

16. The self-tapping implant of claim 13 in which said two cavities have a concave configuration.

17. A self-tapping implant for permanently anchoring in bone, comprising:
    a generally cylindrically shaped body having an externally threaded middle section and an end adjacent said middle section, wherein said end includes three separate flutes disposed around said body with each of said flutes having three separate and distinct cavities for tapping said bone, wherein a first cavity has a generally concave configuration with a primary cutting edge for removing bone chips from said bone and being disposed along a longitudinal axis of said body and having a curvature that directs a smooth flow of bone chips away from said cutting edge, and wherein a second cavity is adjacent said first cavity to provide clearance for said bone chips.

18. An implant, comprising:
    a generally elongated body having external threads disposed along a midsection and a tapping end adjacent said midsection, wherein said tapping end taps bone as said implant is screwed into said bone, said tapping end includes at least two flutes each having a first cavity with a primary cutting edge and a second cavity adjacent said first cavity, wherein said second cavity has a spiral point surface that removes bone chips from said bone and directs said bone chips away from said cutting edge of said first cavity.

19. The implant of claim 18 in which said first cavity has an elongated configuration extending along a longitudinal axis of said implant, and said primary cutting edge is disposed along one side of said first cavity and positioned to remove said bone chips from said bone as said implant is screwed into said bone.

20. The implant of claim 18 in which said second cavity has a volume for accumulating said bone chips removed from said bone.

21. The implant of claim 18 in which said flutes are symmetrically positioned around said tapping end and extend from said spiral point surface toward said midsection.

22. The implant of claim 18 in which said primary cutting edge removes bone chips from said bone as said implant is screwed into said bone.

23. The implant of claim 18 in which said two cavities have a concave configuration.

24. The implant of claim 18 in which said second cavity is below said first cavity.

25. The implant of claim 18 in which said second cavity has a common border with said first cavity.

26. The implant of claim 18 in which said second cavity has a lower end with a spherical configuration and an upper end with a conical configuration.

27. The implant of claim 18 in which said second cavity and said first cavity cut bone simultaneously.

28. The implant of claim 18 in which said second cavity has a secondary cutting edge that is connected to said primary cutting edge.

29. The implant of claim 18 in which said second cavity is parallel to said first cavity with a common border extending between said first and second cavities such that when said primary cutting edge cuts bone chips from said bone said bone chips move away from said primary cutting edge, over said common border, and into said second cavity.

30. An implant, comprising:
a generally elongated body having external threads disposed along a midsection and a tapping end adjacent said midsection, wherein said tapping end taps bone as said implant is screwed into said bone, said tapping end has a spherical end and includes at least two flutes intersecting said spherical end and each having a first cavity with a primary cutting edge and a second cavity adjacent said first cavity such that said two cavities are connected together to direct bone chips through each of said cavities.

31. The implant of claim 30 in which said first cavity has an elongated configuration extending along a longitudinal axis of said implant, and said primary cutting edge is disposed along one side of said first cavity and positioned to remove said bone chips from said bone as said implant is screwed into said bone.

32. The implant of claim 31 in which said second cavity is parallel to said first cavity.

33. The implant of claim 30 in which said second cavity has a volume for accumulating said bone chips removed from said bone.

34. The implant of claim 30 in which said flutes are symmetrically positioned around said tapping end and extend from said spherical end toward said midsection.

35. The implant of claim 30 in which said second cavity has a secondary cutting edge, and said primary and secondary cutting edges remove bone chips from said bone as said implant is screwed into said bone.

36. The implant of claim 30 in which said two cavities have a concave configuration.

37. The implant of claim 30 in which said second cavity is below said first cavity.

38. The implant of claim 30 in which said second cavity has a common border with said first cavity.

39. The implant of claim 30 in which said second cavity has a lower end with a spherical configuration and an upper end with a conical configuration.

40. The implant of claim 30 in which said second cavity has a secondary cutting edge and said primary and secondary cutting edges cut bone simultaneously.

41. The implant of claim 30 in which said second cavity has a secondary cutting edge that is connected to said primary cutting edge.

42. The implant of claim 30 in which said primary cutting edge removes said bone chips and directs them into said second cavity.

43. A self-tapping implant for anchoring in bone, comprising:
an elongated body having a threaded midsection and a tapping end including at least one flute formed having at least two separate and distinct cavities for tapping bone, wherein said first cavity has an elongated configuration with a cutting edge disposed along one side and said second cavity has a somewhat spherical configuration that includes another cutting edge.

44. The implant of claim 43 in which said second cavity has a volume for accumulating said bone chips removed from said bone.

45. The implant of claim 43 in which:
said first cavity has a cutting edge for removing bone chips from said bone as said implant is screwed into said bone; and
said second cavity is disposed next to said first cavity to collect said bone chips.

46. The implant of claim 43 in which said bone chips move away from said cutting edge to said second cavity.

47. The implant of claim 43 in which said cutting edge of said second cavity is disposed below said first cavity to cut bone before said first cavity cuts bone.

48. The implant of claim 43 in which said cutting edges of said first and second cavities cut bone simultaneously.

* * * * *